United States Patent [19]
Hammerslag

[11] Patent Number: 6,155,265
[45] Date of Patent: Dec. 5, 2000

[54] CONTROLLED VISCOSITY DERMAL ADHESIVE

[75] Inventor: Julius G. Hammerslag, San Juan Capistrano, Calif.

[73] Assignee: Hemodynamics, Inc., Irvine, Calif.

[21] Appl. No.: 09/339,146

[22] Filed: Jun. 24, 1999

Related U.S. Application Data

[63] Continuation-in-part of application No. 09/078,944, May 14, 1998, which is a continuation-in-part of application No. 08/991,823, Dec. 17, 1997.

[51] Int. Cl.$^7$ .................................................. A61B 19/00
[52] U.S. Cl. ............................................................. 128/898
[58] Field of Search .................................... 128/898, 897; 623/2, 11, 66; 602/42, 48, 41, 43, 54, 59

[56] References Cited

U.S. PATENT DOCUMENTS

| | | |
|---|---|---|
| 3,527,841 | 9/1970 | Wicker, Jr. et al. . |
| 3,559,652 | 2/1971 | Benitt et al. . |
| 3,759,264 | 9/1973 | Coover, Jr. et al. . |
| 3,995,641 | 12/1976 | Kronenthal et al. . |
| 4,035,334 | 7/1977 | Davydov et al. . |
| 4,268,495 | 5/1981 | Muxfeldt et al. . |
| 4,713,235 | 12/1987 | Krall . |
| 5,154,320 | 10/1992 | Bolduc . |
| 5,222,939 | 6/1993 | Tiefenbrun et al. . |
| 5,234,462 | 8/1993 | Pavletic . |
| 5,248,706 | 9/1993 | Uemura et al. . |
| 5,248,708 | 9/1993 | Uemura et al. .......................... 523/212 |
| 5,254,132 | 10/1993 | Barley et al. . |
| 5,259,835 | 11/1993 | Clark et al. . |
| 5,328,687 | 7/1994 | Leung et al. . |
| 5,350,798 | 9/1994 | Linden et al. . |
| 5,445,597 | 8/1995 | Clark et al. . |

(List continued on next page.)

FOREIGN PATENT DOCUMENTS

| | | |
|---|---|---|
| 491377 | 3/1976 | Russian Federation . |
| WO 96/00760 | 1/1996 | WIPO . |

OTHER PUBLICATIONS

Herrmann, John B., et al., "Comparison of Methods for Determining Biodegradability of Cyanoacrylate Tissue Adhesives"; Research Communications in Chemical Pathology and Pharmacology; vol. 3 No. 1 Jan. 1972; pp. 155–164.

Vezin W.R., et al., "In Vitro Heterogeneous Degradation of Poly (n–alky] α cyanoacrlates)"; Journal of Biomedical Materials Research; vol. 14, 1980; pp. 93–106.

Jaffe, H., et al., "Synthesis and Biovaluation of a Rapidly Biodegradable Tissue Adhesive; 1–2–Isopropylidene Glyceryl 2–Cyanocrylate"; Journal of Biomedical Material's Research, vol. 20, 1986; pp. 213–217.

Tseng, Yin–Chao, et al., "In Vivo Evaluation of 2–Cyanoacrylates as Surgical Adhesives"; Journal of Applied Biomaterials; vol. 1, 1990; pp. 111–119.

Leonard, Fred; "The N–Alky] Alpha Cyanocrylate Tissue Adhesives"; U.S. Army Medical Biomechanical Research Laboratory; Technical Report 6610; May 1966.

"Cab–O–Sil ® Untreated Fumed Silica Properties and Functions"; Cabot Corporation Cab–O–Sil Division Product Brochure; Oct. 1993.

*Primary Examiner*—Dinh X. Nguyen
*Attorney, Agent, or Firm*—Knobbe, Martens, Olson & Bear, LLP.

[57] ABSTRACT

Methods and compositions for closing and sealing a wound, laceration, incision, or other percutaneous opening using an adhesive. In one preferred embodiment, the sides of the percutaneous opening are brought together in apposition and the adhesive is applied to the opening and the skin immediately adjacent thereto. Adhesives used in the methods exhibit sufficient viscosity to substantially prevent flow of the adhesive into the percutaneous opening. In a preferred embodiment, the adhesive is a sealing medium comprising an adhesive component and a microparticulate component. Preferred sealing media comprise cyanoacrylates combined with fumed silica. In such embodiments, the fumed silica is present in an amount sufficient to substantially prevent the medium from flowing into the opening at normal skin temperature.

17 Claims, 3 Drawing Sheets

U.S. PATENT DOCUMENTS

| | | |
|---|---|---|
| 5,514,371 | 5/1996 | Leung et al. .................... 424/78.35 |
| 5,514,372 | 5/1996 | Leung et al. . |
| 5,529,577 | 6/1996 | Hammerslag . |
| 5,530,037 | 6/1996 | McDonnell et al. . |
| 5,550,172 | 8/1996 | Regula et al. . |
| 5,575,599 | 11/1996 | Leung et al. . |
| 5,582,834 | 12/1996 | Leung et al. . |
| 5,684,042 | 11/1997 | Greff et al. . |

CONTROLLED VISCOSITY DERMAL ADHESIVE

BACKGROUND OF THE INVENTION

This is a continuation-in-part of copending application Ser. No. 09/078,944, filed May 14, 1998, which is a continuation-in-part of copending application Ser. No. 08/991,823, filed Dec. 17, 1997, the disclosures of which are incorporated in their entireties by reference herein.

The present invention relates to sealing media used for wound closure. More particularly, the present invention relates to sealing media of the type useful for bonding adjacent sections of skin separated by percutaneous incision or traumatic injury.

Every year, over 10 million traumatic wounds are treated by emergency physicians in the United States. A great many incisions ranging from a few millimeters to several centimeters in length are closed each year by medical personnel. Countless more less serious wounds are treated by non-medical persons, such as athletic trainers, parents of an injured child, or the injured individual himself Small wounds and lacerations may be treated by simply bandaging the wound or by using tape to keep the edges of the wound in apposition. Such methods may be performed with a minimum of time and training, as well as causing little or no additional trauma to the wound or causing the patient additional pain.

More serious wounds or incisions are generally treated by conventional methods such as suturing. Suturing requires the use of a needle and often involves a local anesthetic. Suturing can be costly because it is time-intensive and the procedure requires that the individual performing it have some medical training. Additionally, suturing can be painful and the use of needles may cause further distress for an already traumatized patient, as well as expose medical personnel to potential needlestick injury. Furthermore, because most sutures used topically do not dissolve, the patient generally must make a return visit at a later date for the often uncomfortable procedure of removal of the sutures.

In recent years, cyanoacrylate tissue adhesives have been tried as an alternative for such conventional methods. The most commonly used cyanoacrylates, which include ethyl- and butylcyanoacrylate, have some advantages over suturing, such as faster and less painful closure. They do, however, have several drawbacks. One drawback is that they have a very low viscosity. The low viscosity makes precise application difficult, in that the adhesive flows over areas of the skin surface well beyond the immediate region of the closure and that the adhesive is readily drawn into the wound, effectively creating a barrier between the two tissue surfaces which are desirably rejoined in the natural healing process. Furthermore, certain cyanoacrylate adhesives form a closure which is hard, brittle, and inflexible, and which sets up too quickly to allow for adjustment of the opposing skin surfaces following its application.

Thus, there remains a need for a simple and effective method and composition for effecting wound closure. Preferably, the method and composition can be utilized with minimal training time and risk of error, and will not materially increase complications, immunogenicity, scarring, infection, or other negative factors.

SUMMARY OF THE INVENTION

In accordance with one aspect of the present invention, there is provided a method of closing a percutaneous opening, having a first dermal surface on a first side of the opening and a second dermal surface on a second side of the opening and generally coplanar with the first dermal surface. The method comprises applying an adhesive layer across at least a portion of the first and second dermal surfaces and spanning the opening, wherein the adhesive exhibits a sufficient viscosity to substantially prevent flow of the adhesive into the opening.

In accordance with another aspect of the present invention, there is provided a method of closing and sealing a wound in a patient. The method includes positioning opposing sides of a wound in an adjacent configuration and delivering a wound closure medium comprising an adhesive component and a viscosity enhancing component to the surface of the skin spanning said wound in a quantity sufficient to retain closure of said wound. In the method, the viscosity enhancing component is present in an amount sufficient to substantially prevent the medium from flowing into a gap of about 1 mm or less at normal skin temperature.

In accordance with a further aspect of the present invention, there is provided a method of closing and sealing a wound in a patient. The method comprises the steps of identifying a percutaneous wound having first and second sides, delivering a layer of wound closure media to the surface of skin on each of the first and second sides and across the wound in a quantity sufficient to retain closure and sealing of said would, and restraining the media from entering the wound.

Further features and advantages of the present invention will become apparent to those of skill in the art in view of the detailed description of preferred embodiments which follows, when considered together with the attached drawings and claims.

DETAILED DESCRIPTION OF THE PREFERRED EMBODIMENTS

Figure 1:
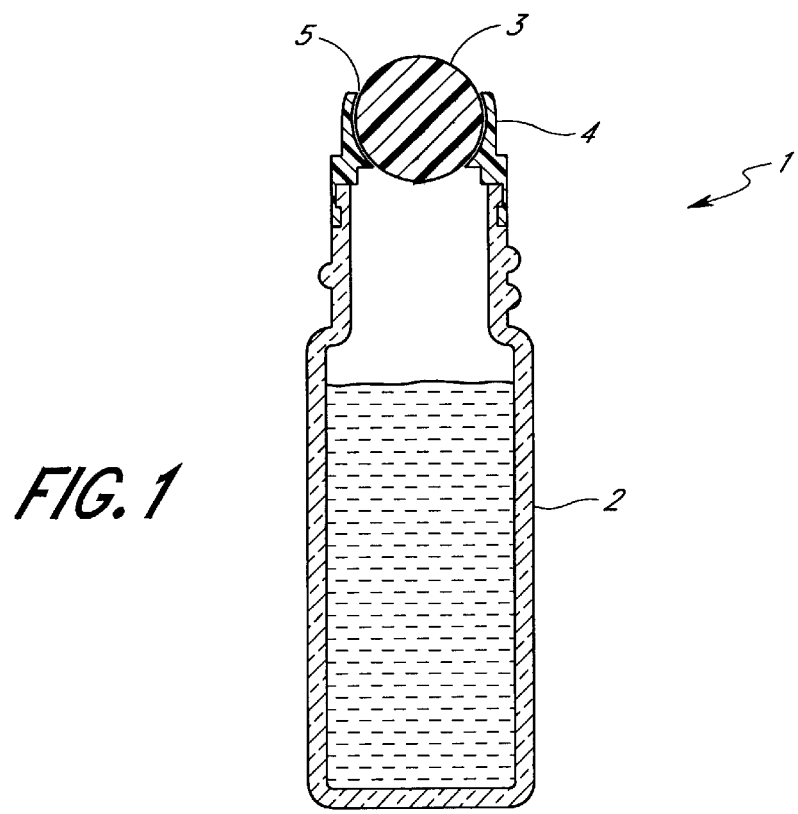
FIG. 1 is a cross-section of a rollerball container-applicator as may be used to apply wound closure media in accordance with the present invention.

Several considerations come into play when a closing percutaneous opening, such as a wound or incision. The considerations include providing a closure having adequate strength to resist opening or rupture and providing a closure which protects the opening but does not at the same time substantially interfere with the normal healing processes. One method which may be used is the application of an adhesive. An adhesive may be used either with or without additional closure means.

When the adhesive used is a liquid, it presents a different set of considerations as compared to solid materials and other conventional methods of closure, such as staples, sutures, and bandages. Several of these considerations have to do with the viscosity of the adhesive.

In discussing the viscosity of the adhesives in the context of the present invention, the viscosity referred to herein is the viscosity of the adhesive at the time it is being applied. Following application, the adhesive will increase in viscosity until the adhesive "sets up" to form the final solid or relatively solid state of the adhesive closure due to physical or chemical mechanisms in the adhesive or adhesive preparation such as curing, cross-linking, polymerizing, and evaporation of solvent. Once the adhesive has set up to form the closure, it will preferably take a solid form, which may be flexible, rubbery or stiff, with firm but flexible closures being preferred.

Adhesives used in accordance with the present invention preferably have a viscosity low enough such that they flow when acted upon by gravity or some other force, such as being squeezed out of a tube. This allows for the adhesive to wet the skin adjacent the opening and also allows for application of the adhesive by a variety of methods. On the other hand, the viscosity of the adhesive during application is preferably not so low that the adhesive becomes runny and flows far beyond the general vicinity of the intended application surface or that it flows into the opening itself. This is an especially important consideration, because if the adhesive flows a substantial distance into the opening, it may block the surfaces which must heal together, and thus may actually impede or prevent the healing process. Seepage into the wound is a significant problem with adhesives known in the art, such as liquid cyanoacrylates which have a very low viscosity and will, when placed on a wound, run into the wound or be drawn therein via capillary action.

To achieve at least some of the properties discussed above, the adhesive used to close a percutaneous opening in accordance with the present invention preferably has a viscosity greater than about 1000 centipoise. Although very high viscosity materials may be used in accordance with the present invention, viscosities of less than about 150,000 are generally used, and it is preferred that the viscosity be less than about 100,000 centipoise such that the adhesive maintains a reasonable amount of workability and ability to flow under pressure. In many embodiments, the viscosity of the adhesive is within the range of from about 40,000 to about 80,000 centipoise.

Especially preferred adhesives are those which have a viscosity such that, when it is placed on the skin, the adhesive will span the gap between the two or more surfaces of the opening with no flow into the opening or without flowing a substantial distance into the opening. The opening spanned without substantial seepage into the wound is generally about 0.1 mm to about 4 mm wide, preferably 0.5 mm to about 1.5 mm wide, and for many applications about 1 mm wide.

When adhesive is used having sufficient viscosity to span an opening as described above, the adhesive can be made to form a thicker layer above the wound than would be possible with a thinner adhesive. This is because the more viscous adhesive will have a greater resistance to flow under its own weight and will thus be more likely to stay in a shape closely approximating that in which it was applied. In one preferred embodiment, the adhesive, when applied to the skin, has the profile seen in FIG. 6. Such a profile may be achieved by using an applicator such as that shown in FIGS. 3 and 4 or by applying a generally rounded bead of adhesive to the skin which then wets the skin surface. This profile of adhesive on the skin, wherein the layer of adhesive 18 forming the closure is relatively thicker in the area generally over the opening 20 between the pieces of skin 19, has advantages in that a thicker layer of a given adhesive will have greater tensile strength than will a thinner layer of the adhesive. The increase in tensile strength of the material forming the closure will provide increased protection against tearing or rupture of the opening following sealing.

If an adhesive having a chemical composition suitable for use in wound closure does not have a viscosity in the preferred range of about 1000 to 100,000 centipoise, this preferred working viscosity may be achieved in a variety of ways. If the desired adhesive has a higher viscosity, such as may be found with a thick gel or rubber-like material, the adhesive may be combined with a solvent of high or moderate volatility to lower the viscosity into the preferred range. The solvent could then evaporate when it comes into contact with the warm surface of the skin.

For thinner materials, which will likely form the great bulk of desirable adhesives, the viscosity should preferably be increased. If an adhesive sets up by means of polymerizing, cross-linking or other curing mechanism, a partially cured adhesive preparation may be used. By using a partially cured adhesive, the viscosity could be brought within a suitable range for application according to the discussion herein. Such an adhesive may be prepared by initiating the curing mechanism and then quenching it, such as by adding an inhibitor. The curing mechanism would then need to be re-initiated prior to application, or immediately thereafter. This type of method could be used for UV-curable adhesives, for which re-initiation could begin by means of a UV lamp or natural sunlight once the adhesive is removed or expressed from its container. This method would also be suitable for adhesives which set up in the presence of water, in that moisture in the air or on the skin could provide the needed water, or the site could be swabbed with water prior to application.

Another method for achieving a suitable viscosity range if the adhesive itself has a low viscosity, is to add particulate matter or other suitable viscosity-enhancing material to the adhesive compound to form a wound closure medium. Suitable wound closure media, also called sealing media, are discussed in greater detail below.

In accordance with the present invention, a sealing medium is used to join adjacent surfaces of skin to effect closure of a wound or incision. The gel or paste sealing media used in accordance with the present invention are typically used as the primary closure modality, to replace conventional sutures or staples. The two sides to a percutaneous incision, for example, can be held together and a layer of sealing gel can be placed on the surface to span the incision. After sufficient polymerization, the gel will provide a strong bond while natural healing processes occur. It is preferred that the sealing media of the present invention are used as the primary method of wound closure, but they may be used in conjunction with other wound closure or tissue fastening systems, such as staples and sutures, or in combination with a support structure such as cloth or gauze.

Although specific closure means and support structures are identified and discussed in this specification, such use of the terms should not be construed as limiting the definitions of these terms. It is the applicant's intention that these terms be given their broad ordinary meanings.

The present invention may be used to effect wound or percutaneous incision closure in a manner that is quick, simple, and effective. The materials and methods of the present invention require little training for their use ani may be used by medical personnel to replace conventional methods of closing wounds. Additionally, they may be used by non-medical persons for use in combination with or as a replacement for conventional home remedies, such as adhesive bandages.

Formulations of sealing media of the present invention preferably comprise a tissue adhesive such as a cyanoacrylate which has been modified to increase its viscosity and, preferably, decrease its polymerization rate. The viscosity of the cyanoacrylate can be increased to a gel or paste form by chemical modification of the cyanoacrylate molecule and/or by the presence of one or more thickening agents. In one embodiment, the sealing medium of the present invention comprises a generally homogeneous mixture of an adhesive compound and a thickener such as a microparticulate component. Any of a variety of other additives can also be added, such as bacteriostatic agents, anti-inflammatory agents, preservatives, stabilizers and the like, as will be understood by those of skill in the art.

Examples of adhesive compounds include cyanoacrylates and fibrin based adhesives. Polymerizable cyanoacrylates that have been cross-linked or co-polymerized with other compounds that may alter elasticity, modify viscosity, aid biodegradation or change some other property of the resulting material may also be used as adhesive compounds in accordance with the present invention. For example, polyacrylic acid having a molecular weight of 200,000 to 600,000 may be cross-linked to a cyanoacrylate to form compounds which may allow the absorbability to be coordinated with the tissue regeneration rate and may feature higher elasticity than cyanoacrylates alone. Absorbability is unnecessary for topical applications, in which the adhesive film will simply fall off in a few days.

Microparticulate components in accordance with the present invention may include silica, and tiny beads or pieces of polymeric materials such as polymethylmethacrylate (PMMA). Preferably, formulations of sealing media comprise cyanoacrylate as the adhesive compound and silica as the microparticulate component.

Among the reasons why cyanoacrylates are preferred are that they have several particular advantages as an adhesive compound. First, they harden almost instantaneously on contact with surfaces having moisture thereon. Thus includes most tissues and surfaces in and on the body of an animal, such as a human. Second, experiments by the inventor indicate that cyanoacrylate sealed vascular punctures can withstand several times the maximum potential systolic pressure, and hence, would not be expected to fail when used to seal most surface wounds. Also, cyanoacrylates are naturally thrombogenic. This is an advantage in certain applications as it promotes the first step in healing.

Preferred adhesive compounds to be used in the media of the present invention include biologically suitable compounds within the cyanoacrylate family. That family includes methyl cyanoacrylate, ethyl cyanoacrylate, n-propyl cyanoacrylate, isopropyl cyanoacrylate, n-butyl cyanoacrylate, isobutyl cyanoacrylate, n-amyl cyanoacrylate, isoamyl cyanoacrylate, 3-acetoxypropyl cyanoacrylate, 2-methoxypropyl cyanoacrylate, 3-chloropropyl cyanoacrylate, benzyl cyanoacrylate, phenyl cyanoacrylate, alkenyl cyanoacrylate, butyl-2-cyanoacrylate, alkoxyalkyl 2-cyanoacrylates, fluorinated 2-cyanoacrylates, and carbalkoxyalkyl cyanoacrylates, depending upon acceptable toxicity and other properties for a given application. More preferably the adhesive compound comprises ethyl cyanoacrylate or butyl-2-cyanoacrylate. These latter two compounds, are available commercially from Loctite Corporation (Hartibrd, Conn.) or Pacer Technology (Rancho Cucamonga, Calif). Other members of the cyanoacrylate family may be commercially available or may be synthesized according to published procedures or analogous methods as is within the abilities of one skilled in the art.

The above-listed members of the cyanoacrylate family, as well as other members of the cyanoacrylate family and other adhesive compounds that fall within the scope of this invention and are not listed above, may differ in their properties when used in a sealing medium. The efficacy, histotoxicity, and other medically relevant properties of above-listed and other members of the cyanoacrylate family can be readily determined by routine experimentation by one of ordinary skill in the art. Such experimentation will enable one skilled in the art to choose optimal cyanoacrylate or other adhesive compounds for use in the media of the present invention, for a desired specific application.

Depending upon the nature of the placement and composition of the two surfaces to be joined, the degree of biodegradability or bioabsorbability desired in the sealing medium employed may vary. For wounds or incisions on the surface of the skin, it may be acceptable to use a sealant medium that is only slowly degradable or substantially nonbiodegradable. Alternatively, if both surfaces are living tissues which are internal, it may be preferable to use a sealing medium that will biodegrade over a period of days or weeks, diminishing as the natural healing mechanisms take hold.

There is a wide variation in the rates and facility of in vivo biodegradation of polymers made from monomers which may be used as adhesive compounds in the present invention. There is also a wide variation in such rates among the members of the cyanoacrylate family, the preferred adhesive compounds of the present invention. Generally, polymers of cyanoacrylates which have substituents that are small and/or contain one or more oxygen-containing functional groups (e.g. ether, ester, carbonyl) appear to have increased biodegradability rates. Cyanoacrylates having long chain alkyl groups lacking in oxygen-containing functional groups as substituents may tend to form polymers which biodegrade more slowly. There are also indications in the literature that the biodegradation rate of cyanoacrylate polymers is affected by the polymer molecular weight and crystallinity of the polymer.

There are several studies of biodegradation rates of polymers formed by various members of the cyanoacrylate family in the scientific and medical literature. It is within the abilities of one of skill in the art to use such information in the literature along with routine experimentation in order to choose a member of the cyanoacrylate family with suitable biodegradation characteristics for use in accordance with the present invention.

Microparticulate silica is commercially available in a variety of different particle sizes. That which is preferred is generally less than about 10 microns, more preferably less than about 1 micron, most preferably 0.01 to 0.1 microns for certain applications. Variations in the quantity and particle size of silica used will result in media which differ in properties, including viscosity and tensile strength. Optimization for particular formulations can be accomplished through routine experimentation.

Among the properties that change with the quantity of silica or other microparticulate modifier used are viscosity and polymerization rate. Increasing the percentage (weight to volume) of silica in the medium will increase the viscosity of the medium in a generally linear manner. Increased viscosity provides for easier application of the media on tissues, as viscous media stay where they are placed and thus decrease the incidence of running or dripping onto other surfaces or tissues, or leaking in between sides of a laceration to be closed. As the viscosity of a given medium is increased, the polymerization rate of that medium concomitantly decreases. Decreased polymerization rates allow more time for a practitioner to place and adjust the surfaces that are to be sealed. Where the polymerization time is short, there can be little if any margin for error before the surfaces are sealed. The longer polymerization time has an additional benefit. Since the polymerization process is exothermic, decreasing the polymerization rate decreases the rate that heat is released by the medium, resulting in a lower temperature in the medium and surrounding tissues during polymerization.

An additional property that may change with added silica, and hence increased viscosity, is the toxicity. An experiment to determine cytotoxicity was performed using standard MEM (minimum essential medium) elution techniques. Two polymers, one formed by a commercial preparation of liquid ethyl cyanoacrylate (Aron Alpha from Toagosci, Ltd.) and the other from a medium of the present invention, a gel comprised of 3% by weight fumed silica (Cabot Corporation, Cab-O-Sil Division, Tuscola, Ill.) in ethyl cyanoacrylate were extracted for 24 hours in MEM. Mouse cells were exposed to the extracts and were examined at 48 and 72 hours for evidence of cytotoxic effects. There was extensive crenation (shrinking or scarring of cells) and 90% lysis observed in cells exposed to the extract of the commercial ethyl cyanoacrylate adhesive. This extract was thus adjudged to be toxic. In contrast, there was no crenation and 0% lysis in cells exposed to an extract of the medium comprising silica, which was thus adjudged to be non-toxic.

Furthermore, joints or closures formed between surfaces by media of the present invention have a greater flexibility and tensile strength than joints formed by their corresponding adhesive components alone, without a microparticulate modifier.

In some embodiments, formulations of sealing media may additionally comprise one or more optional additives, such as polymers, viscosity modifiers, colorants, perfumes, anti-diffusion agents, salts, antibiotics, anti-microbials, stabilizers, desiccants, catalysts, or agents that slow polymerization.

Generally, formulations of sealant media for the present invention comprise generally homogeneous mixtures of at least one adhesive compound with preferably 0.1% to 15% (weight) microparticulate component. Preferred formulations of sealant media for the present invention comprise generally homogeneous mixtures of at least one cyanoacrylate with preferably 0.25% to 8% (weight) silica, more preferably 1% to 5% (weight) silica, most preferably 1% to 3% (weight) silica.

What follows is a discussion of several applicators and methods of applying the adhesives of the present invention. Although the discussion below is largely in terms of wound closure media comprising an adhesive component and a viscosity enhancing component, it is contemplated that any of the adhesives described herein may be used in connection with the devices and methods described.

Any of a variety of containers or devices can be used to apply or deliver media to a wound for closure and sealing. For example, syringes, eyedroppers, compressible bottles or tubes, tongue depressors, spatulas, and the like can be used to deliver media to the site intended for sealing. Media in paste form can be scooped manually from a jar or other container by fingers and manually packed on the wound to effect closure. Additionally, devices designed to deliver sealing media may be used, such as that disclosed in U.S. Pat. No. 5,529,577. Preferably, once they are formulated, media are placed in container-applicators such as those discussed in greater detail below. The choice of application or delivery means may, in part, be determined by the viscosity of the medium employed, which is dependent upon factors such as the viscosity of the adhesive compound, the nature and particle size of the microparticulate component, and the relative amounts of adhesive compound and microparticulate component. The choice of delivery means may also depend on other factors such as the nature, physical structure, and location on the body of the wound to be closed and sealed.

Proper storage of sealing media is an important consideration. For example, if a UV-curing adhesive is used, the storage container preferably prevents penetration of UV radiation, and if a water-curing adhesive is used, a desiccant may be used. Because many cyanoacrylates will polymerize and harden relatively rapidly when stored below a critical volume, it will be preferable for the vessel or reservoir in which the sealing medium is stored to contain more medium than is necessary to seal a typical site if a cyanoacrylate adhesive is used. Preferably, the storage vessel or reservoir in a single-use container or container-applicator will contain a minimum of 1 to 5 grams, more preferably 3 to 4 grams of medium or more to maintain the cyanoacrylate component of the medium in a generally unpolymerized state in the storage vessel or reservoir prior to use. For multiple-use containers or container-applicators, the reservoir preferably contains 1 to 50 grams, more preferably 15 to 30 grams of medium. The total volume of medium, the desiccation measures, and the sealing structures in the container or container-applicator may be optimized by one of skill in the art to provide enhanced shelf life.

The wound closure media of the present invention are preferably stored and applied using a container-applicator. A container-applicator has two basic parts: (1) a storage area or reservoir which holds the media and protects it from air, water and contaminants; and (2) the applicator which comprises a specially shaped tip designed to aid in application of media.

The reservoir is preferably both air-tight and water-tight, and keeps the media within free from contaminants. The reservoir may contain a desiccant material to keep the media free of water, which would cause polymerization of the preferred cyanoacrylate-based media. Reservoirs may be of any shape, although shapes which provide for a smooth internal flow of media, such as cylindrical or pyramidal shapes, are preferred. The size of the reservoir may vary within a wide range, but is preferably slightly larger than the volume of media which will be placed inside the reservoir to minimize the amount of gas within the reservoir. The reservoir may be made from any of a variety of medical grade materials, such as plastics, that is suitable for the storage of cyanoacrylates as is known in the art. The reservoir may be either rigid, collapsible, or compressible. Use of a compressible or collapsible reservoir allows the user to have greater control over the rate at which media is expressed, as exertion of pressure on a compressible or collapsible reservoir would place a force on the on the media causing it to flow at a faster rate than it would in the absence of such pressure. The compressible or collapsible reservoir design is especially preferred for highly viscous or gel-like media for which the force of gravity may not be strong enough to cause a flow of media through an applicator sufficient to close a wound. Collapsible reservoirs which retain their collapsed shape have the additional advantage of reducing the amount of air which enters the reservoir following use. This advantage of collapsible containers is of greater importance in multiple-use (reuseable) devices, wherein media is preferably kept relatively free of potential contaminants between uses.

Applicator tips can be of any of a number of shapes, sizes, and configurations. They are preferably fairly rigid and may be made out cf any material which is compatible with the media formulation, preferably plastic. The choice of a proper applicator tip for a given application will depend on factors such as the viscosity of the media, the desired application rate of the media, the nature of the wound, the placement of the wound on the body, and the physical structure of the wound.

The container-applicators of the present invention may be either single-use or multiple-use devices. For most applications, single-use container-applicator devices are preferred. This preference arises because the risk of cross-contamination between wounds or patients is practically eliminated when a new device is used for each closure. As an alternative to the single-use embodiment, a container or reservoir containing enough media for multiple closures may be configured to accommodate replaceable tips. In such an embodiment, at the place whereon the replaceable tips connect with the reservoir, the reservoir would preferably have a means such as a valve, septum or sealing gasket which allows the reservoir to be sealed in the absence of an applicator tip. Placing an applicator tip on the reservoir would cause the valve to open, allowing media to flow out from the reservoir. In this manner, one reservoir containing enough media to close several wounds could be used over a period of hours, days or weeks. This embodiment would also allow the user to use one reservoir with applicator tips of varying shapes and sizes chosen to best accommodate the needs of different wounds.

Two specific embodiments of container-applicators are depicted in the drawings and detailed below. These embodiments are presented as illustration only, as it is the inventor's intention that the invention be limited only by the scope of the attached claims, and not exclusively to the embodiments disclosed with particularity herein.

One preferred embodiment of container-applicator is the rollerball container-applicator 1 depicted in FIG. 1. The reservoir 2 mall be either rigid, compressible, or collapsible and may be made out of any material suitable for the storage of cyanoacrylates, as is known in the art. The applicator tip portion of the container-applicator comprises a ball 3 and a cuff 4. The ball 3 is held loosely within the, cuff 4 so that the ball 3 is free to rotate in any direction, but not so loosely as to allow the ball 3 to be removed or fall out when the container-applicator 1 is inverted. The size of the gap 5 formed between the ball 3 and the cuff 4 can be varied to accommodate a wide range of viscosities of media and desired flow rates. For low viscosity media, a relatively small gap 5 would be preferred to allow the media to flow out around the ball at a reasonable rate during application, whereas for high viscosity gel-like media a larger gap 5 would be required to allow a reasonable flow of media around the ball 3. Similarly, the gap 5 can be varied to achieve a desired application rate for media of a particular viscosity. For media of a given viscosity, a large gap 5 would provide a higher flow rate for the media than a smaller gap 5. Furthermore, use of a compressible or collapsible reservoir 2 allows for additional control over the rate at which media is expressed, as exertion of pressure on the compressible reservoir increases the pressure on the media causing it to flow through gap 5 at a rate faster than that for the same media in the absence of exerted pressure, regardless of viscosity.

Figure 3:
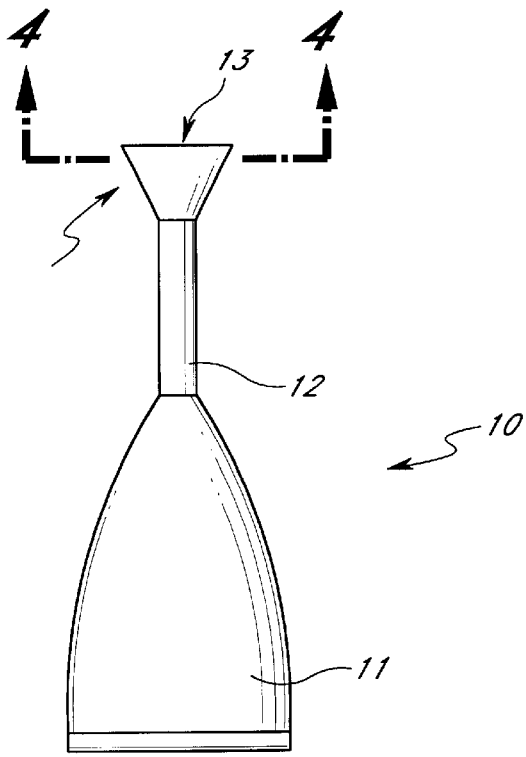
FIG. 3 is a view of an alternate container-applicator for use in accordance with the present invention.

A second embodiment of container-applicator is that depicted in FIG. 3. This embodiment comprises a container such as pyramidal reservoir 11 and an applicator tip 12. The container-applicator 10 may further comprise a one-time removable or breakable sealing tip or cap as described below. In the illustrated embodiment, the media flows from the reservoir 11 through a tubular extension 12 and out to the application site through an opening 13 in the flared distal end of the applicator tip 14. In one preferred embodiment, the length of the extended portion 12 of the applicator tip 14 is preferably 0.1 to 10 cm long, more preferably 0.5 to 2 cm, but can be readily optimized in view of an intended use for the applicator 10. The largest cross-section of the flared end can also come in a wide range of sizes, preferably from 0.5 to 5 cm, generally less than 2 cm, but it is most preferably chosen to be a little larger than the width of the wound to be closed. The configuration of the opening 13 may be a narrow elliptical or rectangular slot or other configuration suited for the end use. The reservoir 11 is preferably compressible or collapsible to allow for greater control in the rate at which the media is expressed from the opening 13.

Figure 4:
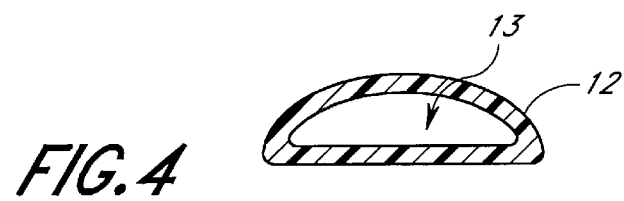
FIG. 4 is a cross-section of the container-applicator of FIG. 3.

In one embodiment, the distal opening 13 of the applicator tip 14 has a shape like that shown in FIG. 4. During application, the flattened side is placed towards the skin to maximize the area of applicator-skin contact. This semi-elliptical or other concave shape of the opposing side of opening 13 results in application of a rounded strip of sealing medium as the tip 14 is drawn across the surface of the skin. Center thickness on the order of at least 2 times and often as much as 3 or 5 times or greater the edge thickness are preferably achieved. This shape optimizes adhesive tensile strength across the top of the wound. In general the combination of thickness and inherent adhesive characteristics for a particular sealing media should be optimized to provide both a sufficient bond to the skin as well as sufficient tensile strength to resist tearing under reasonably anticipated forces encountered by normal activities of the patient.

Figure 5:
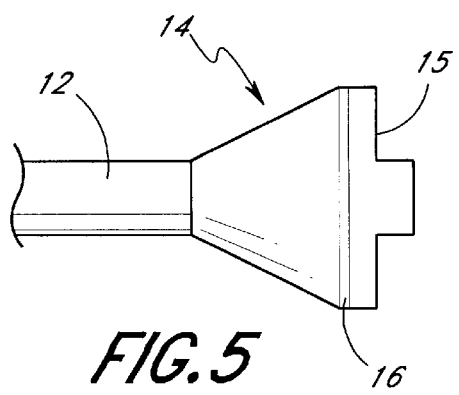
FIG. 5 is a blown-up view of the applicator tip of the container-applicator of FIG. 3 showing the placement of a break-away seal tip.

The applicator tip of the container-applicator may further comprise a removable or breakable sealing tip. One embodiment of a breakable sealing tip, which may be used for a single-use device, is shown in FIG. 5. The applicator cap 15 forms a solid covering for the opening of the applicator tip (14 in FIG. 5). The applicator cap 15 is preferably of the same material as the applicator tip 14, the two parts meeting at a breakline 16. In one embodiment in which the tip 14 and cap 15 are integrally formed, the breakline 16 is characterized by scoring or other means which weakens the junction and allows the two parts to be easily separated by grasping the two parts (12 and 15) in either hand and bending or tearing the pieces apart to expose the opening 13 in the applicator tip 12 through which the media is expressed. The cap 15 can alternatively be press fit or threadably engaged within or over the distal tip 14 and retained by friction as will be apparent to those of skill in the art.

Alternatively, a single-use device may comprise a reservoir wherein the opening through which the media flows is covered with a peelable or puncturable plastic film or metal foil. In one such embodiment, the foil or film is peeled back or pierced prior to positioning the applicator and sealing the wound. In another embodiment, the applicator portion has a proximally extending point or projection which pierces the foil or film as it is threaded onto or otherwise secured to the reservoir.

One embodiment of container-applicator is a single-use, sterile wound closure device. Preferably such a device has a pierceable or removable tip seal. The container portion of the preferred single-use wound closure device is sized to hold preferably from 2 to 10 grams, more preferably 2 to 5 grams of wound closure media, depending upon the intended use. The container may be of any of a variety of standard container shapes, and is preferably compressible or collapsible so that the user may control the rate at which the media contained therein is expressed by varying the pressure exerted on the walls of the container.

The single-use sterile wound closure device is prepared by first taking a clean container that will serve as the reservoir and filling it with wound closure media comprising an adhesive component and a microparticulate component. The reservoir is then sealed. Sealing the reservoir is preferably done by affixing an applicator tip with a removable seal to the reservoir, or by securing a pierceable septum to the container. The container-applicator, with the wound closure media sealed inside, is then sterilized by methods known to those skilled in the art which may be used on the materials from which the container-applicator is made and which will also not react with the adhesive component of the media.

In the alternative, the pieces which comprise the container-applicator can be pre-sterilized, and the device filled and sealed in a sterile or ultra clean environment. This is potentially a viable method, as the preferred formulation of wound closure media, that comprising cyanoacrylate and silica, is generally not supportive of the growth of microorganisms.

The use of reusable coverings for applicators or applicator openings, such as caps, plugs, valves, or the like are also contemplated. Use of this type of covering would allow a container or container-applicator to be used several times before it is discarded.

The containers, applicators, and container-applicators disclosed above may be used alone, in combination with a support structure, such as a piece of cloth, gauze or mesh, or in addition to some other conventional securing means such as sutures or staples. Support structures can provide an extra measure of strength and protection for the wound, while use of a sealing medium with sutures or staples can reinforce and thoroughly seal the joint to help prevent rupture, protect the joint from abrasion, or keep it free of debris. Similarly, for a deep or penetrating wound or surgical incision, the innermost tissues may be joined by dissolvable sutures while the exterior surface is joined using media according to the present invention.

Closure of a wound may also be effected by the use of a device comprising a support structure impregnated with media. In such a device, the support structure, comprising cloth or gauze, has a sufficient quantity of media imbedded therein to allow for closure and sealing of a wound. Preferably, each device is individually sealed within air-and-water-tight packaging such as a plastic or foil pouch until use. Although the application and use of such a device would be very similar to a conventional adhesive bandage, it has several advantages. The media impregnated support structure will adhere to the wound for a much longer time than a conventional adhesive bandage and provide a better barrier to water, dirt, and abrasion. The media impregnated support structure would be especially suitable for use on children, as it would keep the wound cleaner and prevent the child from disturbing the wound and hampering the healing process.

Generally the methods of the present invention proceed by delivering the appropriate adhesive or closure medium to the percutaneous opening. Following application, the medium or adhesive is allowed to set up. Methods of the present invention may optionally include steps of bringing the sides of the wound into opposition, applying another closure modality to be used in conjunction with the medium or adhesive, and/or holding the surfaces together until the medium or adhesive has adequate strength to hold the opening closed.

Figure 6:
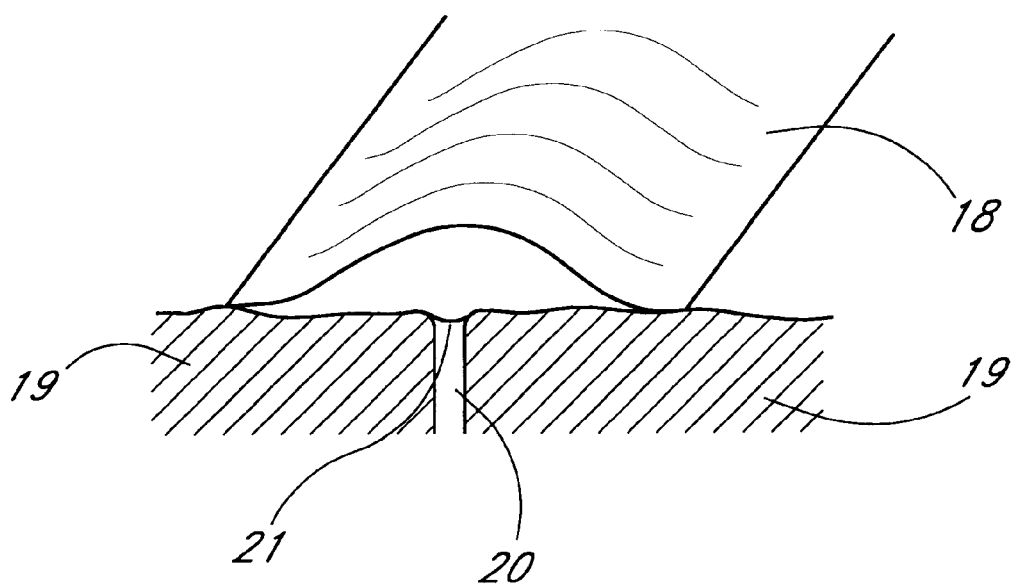
FIG. 6 is a cross-section of a percutaneous opening or wound which has been closed and sealed according to the present invention.

Preferably, the adhesive or medium, when applied, takes on a bell-curve type shape as shown in FIG. 6. This shape is advantageous in that it places the thickest part of the layer, and thus the strongest part of the layer, over the opening in the skin to provide enhanced resistance to tearing, rupture, or other stress or damage to the opening following closure. The added protection provided by a thicker layer may aid in speeding the healing process and allowing for a minimum of scarring. The adhesive or medium may be applied such that the thickness over the percutaneous opening is at least about 0.1 mm, often from about 0.5 mm to 4 mm thick, or from about 1.0 to 2.5 mm thick.

Also in a preferred method, an adhesive or closure medium is used for which the setting up process of the adhesive is enhanced by the presence of water. Prior to application of the adhesive or closure medium, water is placed on the skin in the general area of the wound or opening. This may take any of a variety of forms, including a spray or mist of water or saline, application of an aqueous antibacterial compound such as betadine, or wiping the area with an alcohol/water prep pad. The water which remains on the surface then helps or increases the rate at which the adhesive sets up on the wound.

Initiators, cross-linkers, catalysts, and other compounds which aid an adhesive or closure medium in setting up may be applied in a similar manner, provided that they would not irritate the open wound, or cause other undesirable side effects.

When applying media of the present invention, the surfaces of the wound, laceration, percutaneous incision, or the like intended for closure are brought in contact with each other by use of the fingers, forceps, or a similar device. A sufficient amount of medium is delivered to the surface so that proper sealing and closure retention will occur. When sealing the joint formed by the sides of the wound, laceration, or percutaneous incision, the medium is applied to the exterior surface of the wound and allowed to polymerize so that it forms a film over the entire wound. Preferably, media are applied in a manner to minimize the amount of medium which seeps between the edges of a wound. The amount of sealing medium to apply in any given case, and thus the area and thickness of the resulting film, may depend on several factors including placement of the wound on the body, depth of the wound, tissue sensitivity to the media, and the like. Media may be applied alone or in combination with a support structure or a more conventional securing means such as sutures. Through routine experimentation, however, one of skill in the art will be able to exercise clinical judgment to determine an appropriate quantity of medium to provide effective closure for a particular procedure.

Methods of the present invention are preferably directed toward closing and sealing a wound by sealing and securing together adjacent tissues, such as opposing pieces of skin, in a patient. The need for closure of such a wound may arise during surgical procedures, as a result of percutaneous incision. The need may also arise as a result of traumatic injury resulting in a laceration or other wound which breaks the skin.

Generally, a method of closing a wound, laceration, percutaneous incision, or the like proceeds by first assessing what type of closure or combination of closures is proper for a wound given factors such as the size, depth, and location of the wound as well as an assessment of the overall needs and requirements of the patient. Such assessments are routinely done by those skilled in the medical arts. In a non-clinical setting, the assessment step will likely be much more cursory.

Next, a suitable formulation of sealing medium, an applicator, and a method of application are chosen. These three choices are somewhat interconnected, as the choice of a particular applicator constrains the method of application, and a particular formulation of media may constrain the type of applicator or method of application which can be used, and vice-versa.

The choice of a suitable formulation of wound closure medium comprising an adhesive compound and a microparticulate component, as disclosed herein, may depend upon characteristics of a medium such as its viscosity, biodegradability and rate thereof, resulting tensile strength upon polymerization, flexibility when polymerized, histotoxicity, and polymerization rate. Specific characteristics may be desired to fit clinical needs as dictated by factors such as the size of the wound, the amount and rate of bleeding from the wound, the location of the wound on the body, and potential stress on the sealed wound.

The choice of applicator and method of application may, in part, be determined by factors such as the composition, viscosity, and polymerization time of the medium, and the geometry, size and placement of the application site. Such a choice may also be constrained by the tools and devices available to the user. Examples of preferred applicators are disclosed above and examples of preferred methods of application are described below.

Next, the wound may need to be prepared before closure. Activities involved in wound preparation are highly situational, but are routinely done by those skilled in medicine, nursing, and related arts. Wound preparation may involve tasks such as removal of debris, dirt, oil, or excess tissue from the wound, application of pressure or similar measures to bring about the cessation of bleeding, cleansing the wound, application of an antimicrobial preparation, use of a conventional closure means such as sutures, and other such tasks. In a non-clinical setting, the patient or use may also perform some of these same tasks.

If the surfaces of the wound naturally pull apart, it may be advantageous to bring the two surfaces into contact with each other and align them by use of the fingers, support structure, forceps or other suitable medical instrument. In such a case, the two surfaces are preferably held together as the medium is applied and afterwards until sufficient polymerization has taken place to allow the closure to be self-supporting. Alternatively, the two surfaces may be brought together by sutures, staples;, tape or other securing means and then further sealed by application of a chosen medium. Such methods may allow for eventual scarring of the opening to be minimized. In wounds for which the skin is not separated, this step may be skipped.

The chosen medium is then applied using the applicator and method chosen in an earlier step. The entirety of media application is preferably done within a limited period of time, as the strength of the closure formed by two or more successive applications of media (wherein one application has been allowed to polymerize before the next application) may not be as strong as the closure formed by one application allowed to polymerize to form a single layer on the skin surface. Media is applied in a quantity sufficient to effect wound closure and sealing. More may be applied, if desired, to increase the strength of the closure as discussed above, or likewise a support structure may be applied. Determination of quantity of media applied can be determined by routine experimentation and exercise of clinical judgment. Specific methods of application involving the use of container-applicators are discussed in the paragraphs which follow.

Figure 2:
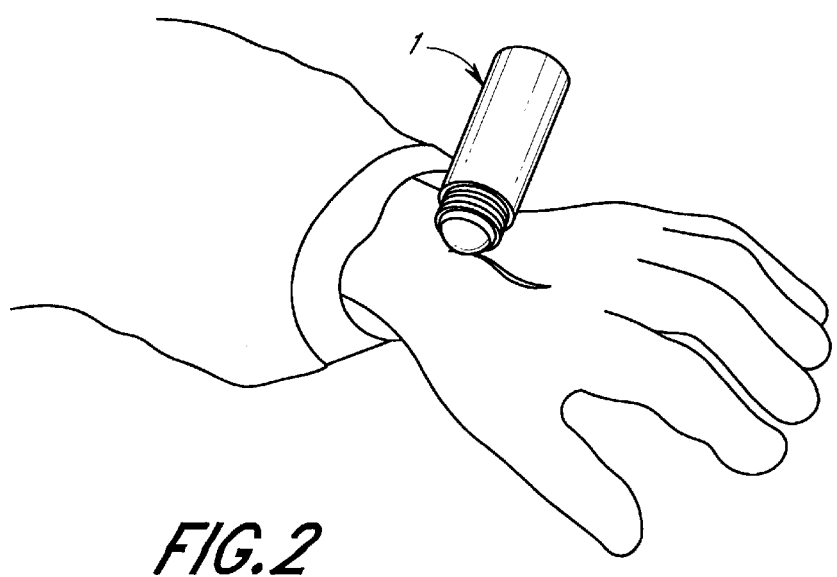
FIG. 2 depicts the use of a rollerball container-applicator of the type in FIG. 1 to deliver wound closure media to a topical wound to effect closure in accordance with the present invention.

One specific method of application is that involving the use of the rollerball container-applicator pictured in FIG. 1. To use this container-applicator, first any sealing means is removed or broken. Then, as depicted in FIG. 2, the container is tipped so that the rollerball is pointing in a generally downward direction and the bottom of the reservoir portion is pointing in a generally upward direction. Such orientation of the container-applicator facilitates the flow of media towards the rollerball applicator portion through which it may then be applied to the wound. Preferably the media is applied by moving the container-applicator back and forth over the surface of the wound and surrounding skin areas while keeping the rollerball in contact with the wound at all times. Although a back and forth movement is preferred, any movement of the applicator which serves to deliver the media to the intended site without disturbing the wound itself is contemplated.

If the reservoir portion of the container-applicator is compressible or collapsible, the rolling of the applicator over the surface of the skin can be accompanied by squeezing or otherwise compressing the walls of the reservoir. With such a collapsible or compressible reservoir, the rate of flow of media and therefore the amount of media delivered, is proportional to the amount of pressure applied to the walls of the reservoir. The quantity and rate of media delivery can thus be controlled by the user.

Another specific method of application is that using a container-applicator of the type depicted in FIG. 3. To apply media, first any sealing means such as a foil seal, peel-away thin film or breakable tip is punctured or removed to allow for flow of media. The applicator tip is preferably placed on or slightly above the surface of the wound to be sealed. If a semi-elliptical tip is used, such as that pictured in FIG. 4, the flattened side is preferably placed closest to the skin. The media is then allowed to flow through the applicator and onto the surface of the skin forming a profile such as shown in FIG. 6. Preferably, the reservoir portion comprises collapsible or compressible walls such that the user may exert pressure on the walls to facilitate the delivery of media to the skin, and thus control the rate at which the media is expressed from the applicator tip. The tip is moved over the surface of the skin, following the contours of the wound, resulting in the deposition of a strip of media on the skin covering the wound. Additional strips may be laid down in a similar manner to thicken or expand the area of media coverage.

In accordance with another embodiment of the present invention, the reservoir is provided as a separate component from the applicator tip. In this embodiment, the reservoir is provided with a pierceable seal or septum, such that a unit volume of media can be sealed within the reservoir. Pierceable septums or seals comprising silicone, other polymeric materials known in the medical industry, as well as metal foils or thin polymeric films may be utilized, as will be apparent to those of skill in the art in view of the nature of the complimentary piercing structure on the applicator tip.

The detachable applicator tip comprises an applicator surface on a distal side thereof, and a cannula, needle or other piercing structure projecting proximally from a proximal side thereof. A retention structure is preferably also provided, for securing the applicator tip to the reservoir. In one embodiment, the retention structure is an axially extending annular flange having a thread on the radially inwardly or outwardly facing surface thereof, for threadably engaging the top of the reservoir. Any of a variety of other retention structures can be utilized, as will be apparent in view of the disclosure herein.

Prior to use at the clinical site, the applicator tip is secured to the reservoir such that the proximally extending piercing member on the proximal side of the applicator tip pierces the septum or other seal on the reservoir, thereby placing the contents of the reservoir in fluid communication with the distal applicator surface. This embodiment is particularly suited for a one-time use disposable device. The applicator surface can be of any of a variety of structures disclosed elsewhere herein, such as a rollerball, or a specially configured opening such as a slot, for expressing a thin layer of sealing media over the surface of the tissue on either side of a wound.

Any of the foregoing methods may be combined with the application of a support structure such as gauze. A layer of media is first applied to the wound, onto which gauze or other support structure is affixed, the media acting to secure the gauze in place. More media may then be applied over the gauze to further secure it and strengthen the closure. In the alternative, gauze may be first placed over the wound and then covered and secured to the wound by subsequent application(s) of media as described above. In either case, alternate layers of media and gauze may be applied to form a flexible, reinforced structure which effects closure of the wound and sealing.

As an alternative to the method discussed above, a prepackaged media-impregnated support structure may be applied to the wound to achieve closure. Such a device, as described above, is preferably packaged in a sealed pouch and comprises a support structure, such as a section of cloth, that is saturated with a quantity of media sufficient to allow for attachment of the support structure and effect closure of a wound or section of a wound of a size corresponding to the size of the support structure. Closure of a wound using such a device is somewhat comparable to using a common adhesive bandage and is particularly well-suited for nonclinical use. First, the pouch containing the device is opened and the device removed therefrom. The device is then placed over the surface of the wound and then pressed into place to ensure good contact between the device and the skin. If additional coverage is required or desired, additional devices may be applied. When more than one device is used, they are preferably applied within a short time of each other so that they polymerize at nearly the same time.

Although the present invention has been described in terms of certain preferred embodiments, and certain exemplary applications, it is to be understood that the scope of the invention is not to be limited thereby. Instead, the inventor intends that the scope of the invention be limited solely by reference to the attached claims, and that variations on the formulation and applications disclosed herein which are apparent to those of skill in the art will fall within the scope of the invention.

What is claimed is:

1. A method of closing a percutaneous opening, having a first dermal surface on a first side of the opening and a second dermal surface on a second side of the opening and generally coplanar with the first dermal surface, the method comprising the step of:

applying an adhesive layer across at least at portion of the first and second dermal surfaces and spanning the opening, wherein the adhesive exhibits a sufficient viscosity to substantially prevent flow of the adhesive into the opening.

2. A method as in claim 1, wherein the viscosity is within the range of from about 1000 to about 100,000 centipoise.

3. A method as in claim 2, wherein the viscosity is within the range of from about 40,000 to about 80,000 centipoise.

4. A method as in claim 1, wherein the viscosity is at least about 1,000 centipoise.

5. A method as in claim 4, wherein the adhesive comprises an adhesive component and a viscosity enhancing component.

6. A method as in claim 5, wherein the adhesive component comprises a nonbiological monomer.

7. A method as in claim 6, wherein the adhesive component comprises a cyanoacrylate.

8. A method as in claim 5, wherein the viscosity enhancing component comprises silica.

9. A method as in claim 1, wherein the adhesive layer has a thickness over the opening of at least 1 millimeter.

10. A method of closing and sealing a wound in a patient, comprising the steps of:

positioning opposing sides of a wound in an adjacent configuration; and delivering a wound closure medium comprising an adhesive component and a viscosity enhancing component to the surface of the skin spanning said wound in a quantity sufficient to retain closure of said wound, said viscosity enhancing component being present in an amount sufficient to substantially prevent the medium from flowing into a gap of about 1 millimeter or less at normal skin temperature.

11. A method as in claim 10, further comprising a step of applying an aqueous solution to the wound prior to the delivering step.

12. A method as in claim 10, further comprising the step of permitting the medium to polymerize following the delivering step.

13. A method as in claim 11, wherein the medium has a prepolymerization viscosity of at least about 1000 centipoise.

14. A method of closing and sealing a wound in a patient, comprising the steps of:

identifying a percutaneous wound having first and second sides;

delivering a layer of wound closure media to the surface of skin on each of the first and second sides and across the wound in a quantity sufficient to retain closure and sealing of said wound; and restraining media from entering the wound.

15. A method as in claim 14, wherein the restraining step comprises providing the wound closure media with a sufficient viscosity to extend in a layer across the wound, while substantially preventing the media from entering the wound.

16. A method as in claim 15, wherein the viscosity is at least 1000 centipoise.

17. A method as in claim 16, wherein the viscosity is at least about 40,000 centipoise.

* * * * *